United States Patent [19]
Voser et al.

[11] Patent Number: 5,942,559
[45] Date of Patent: Aug. 24, 1999

[54] DENTAL LIGHT-CURING OPAQUER

[75] Inventors: Dieter Voser; Gerhard Zanghellini, both of Schaan; Volker Rheinberger, Vaduz, all of Liechtenstein

[73] Assignee: Ivoclar AG, Liechtenstein

[21] Appl. No.: 08/918,060

[22] Filed: Aug. 25, 1997

Related U.S. Application Data

[60] Provisional application No. 60/027,057, Sep. 30, 1996.

[30] Foreign Application Priority Data

Aug. 26, 1996 [DE] Germany .............. 196 34 460
Sep. 3, 1996 [DE] Germany .............. 196 35 667

[51] Int. Cl.⁶ .......................... A61K 6/00; A61K 6/027; A61K 6/083; A61K 6/08
[52] U.S. Cl. ............................ 523/115; 523/116
[58] Field of Search ............... 525/308; 523/115, 523/116

[56] References Cited

U.S. PATENT DOCUMENTS

| | | | |
|---|---|---|---|
| 2,533,196 | 12/1950 | Pace . | |
| 4,389,507 | 6/1983 | Podszun et al. | 524/460 |
| 4,500,658 | 2/1985 | Fox | 523/117 |
| 4,563,153 | 1/1986 | Schaefer | 433/223 |
| 4,861,818 | 8/1989 | Timmerman et al. | 524/460 |
| 5,276,070 | 1/1994 | Arroyo | 523/117 |
| 5,512,610 | 4/1996 | Lin | 523/116 |

FOREIGN PATENT DOCUMENTS 0 011 190 A1  5/1980  European Pat. Off. .

OTHER PUBLICATIONS

Falbe et al., "Römpp Chimie Lexikon," Georg Thieme Verlag Stuttgart, New York pp. 3438–3442 (1991).

*Primary Examiner*—Jeffrey C. Mullis
*Attorney, Agent, or Firm*—Nixon, Hargrave, Devans & Doyle LLP

[57] ABSTRACT

A dental light-curing opaquer is described which is characterized by a content of cross-linked bead polymerizate with incorporated colored pigment and of polymerizable polyfunctional monomer and which is highly suitable for covering metallic surfaces of dental restorations.

18 Claims, No Drawings

DENTAL LIGHT-CURING OPAQUER

This application claims the benefit of U.S. Provisional Application Ser. No. 60/027,057, filed Sep. 30, 1996.

FIELD OF INVENTION

The invention relates to a dental light-curing opaquer which in particular has a high covering power and yet good polymerizability into deep layers and is therefore suitable advantageously for covering metallic surfaces of dental restorations.

BACKGROUND OF THE INVENTION

So-called opaquers, which are also referred to as opaque base masses are used in the covering of metallic tooth crowns or bridges. The opaquers serve to cover the metal structure of the dental restorations, in order that the dark metal can be prevented from showing through and consequently the colour of the natural teeth can be simulated by the relatively thin veneer which is subsequently applied. In addition to a high covering power, the opaquer must also have good adhesion both to the metal structure and to the veneer so that the final tooth restoration is stable in itself.

Dental opaquers are known from the state of the art.

Thus DE-C-33 32 179 describes photopolymerizable dental opaquers which contain a photopolymerization catalyst and a mixture of zirconium dioxide and titanium dioxide as pigment. The opaquer is applied to a metal structure as a thin layer and then cured with light. The metal structure covered with the opaquer is then veneered with plastic and cured for example to form a tooth crown. However, a satisfactory through-hardening of the opaquer is not achieved.

Known from DE-C-41 19 483 are pasty opaque base masses for ceramic and plastic veneers which are fired on at high temperature and which contain glass powder, plus zirconium dioxide as opacifier. Colour pigments are optionally added to the base masses in order to colour them.

It is also known from the state of the art to use bead polymerizates as a component of tooth filling compositions or of materials for producing prostheses.

Thus EP-B-11 186 describes bead polymerizates of viscous dimethacrylates which can be used as filler in pasty dental masses.

EP-B-11 735 and EP-B-11 734 describe pasty X-ray-opaque tooth filling masses which contain bead polymerizates provided with filler. Used as fillers are, for example, barium sulphate and silicon dioxide. However, coloured pigments are not present in the bead polymerizate.

Furthermore, EP-B-84 769 describes cross-linked bead polymerizates which in particular contain silicon dioxide as filler, but again contain no coloured pigments. The bead polymerizates are used as a component of tooth filling materials, being unsuitable for covering materials which are coloured in an undesired way, such as metals, since they are highly transparent.

Cross-linked bead polymerizates filled with fillers and their use as filling means in pasty dental masses are also known from EP-B-11 190. Coming into consideration as fillers are in particular magnesium hydroxide carbonate, titanium dioxide, barium sulphate, zirconium dioxide and silicon dioxide. However, neither the incorporation of coloured pigment into the bead polymerizates nor the use of the bead polymerizates as a component of dental opaquers are described.

Finally, U.S. Pat. No. 4,500,658 discloses X-ray-opaque acrylic bead polymerizates which can be used to prepare dental prostheses. The X-ray opacity of the polymerizates is effected by incorporated X-ray-opaque pigment. When the polymerizates are processed to form dental prostheses, curing takes place by heat and not by irradiation with light. Furthermore, it is also not disclosed to use the X-ray-opaque polymerizates as dental opaquers for covering metal structures in the preparation of crowns or bridges.

In the case of known opaquers which are cured by light, the particular problem occurs that, as a result of their high content of covering pigments, such as $TiO_2$ and $ZrO_2$, they only cure to an unsatisfactory extent when irradiated with light. This is a difficulty which naturally does not occur in the case of heat-curing materials. A reduction in the content of covering pigments is not possible since they are necessary for good covering power. Therefore two requirements, namely high covering power and complete curing by light, are to be met which are contrary to each other since the pigments prevent the penetration of light into deeper layers of the applied opaquer, thereby preventing a complete polymerization.

Thus it is known in the case of conventional light-curing paste opaquers that they often cure only on the top layer and are soft and unpolymerized underneath.

Another problem arising with conventional paste opaquers is that they tend to separate if stored for an extended period into a filler-rich and a filler-poor phase.

It is therefore the object of the invention to provide a dental light-curing opaquer which, despite a high covering power, can be cured by light even in deeper layers and which does not exhibit separation problems even if stored for an extended period.

SUMMARY OF THE INVENTION

This object is achieved by the dental light-curing opaquer.

The invention furthermore relates to the use of the opaquer.

DETAILED DESCRIPTION OF THE INVENTION

The dental light-curing opaquer according to the invention contains the following components:

(a) cross-linked bead polymerizate into which a coloured pigment is incorporated, and (b) polymerizable polyfunctional monomer, with the proviso that the quantity of (a) used is not completely soluble in the quantity of (b) used.

The bead polymerizates used are preferably based on at least one (meth)acrylic acid ester.

Advantageous bead polymerizates (a) contain 1 to 40, in particular 5 to 20 and particularly preferably 10 to 15 wt. % of incorporated coloured pigment, relative to the quantity of bead polymerizate.

It has also proved to be advantageous that the bead polymerizate has a degree of cross-linking of 10 to 90, in particular 20 to 80 and particularly preferably 40 to 60%.

Typically, the bead polymerizate is present in the form of particles with an average particle size of 10 to 100 and in particular 12 to 30 $\mu m$, based on the number of particles.

Customary coloured pigments suitable for colouring dental materials can be used as coloured pigment. Particularly preferred are ultramarine blue; iron oxide pigments; coloured pigments based on cobalt, aluminium, chromium, nickel and/or zinc oxides; and/or organic coloured pigments. Particularly preferred are red and yellow iron oxide pigments. Black and white pigments, such as $ZrO_2$ or $TiO_2$, are not suitable according to the invention as coloured pigments and are therefore not covered by the term "coloured pigments".

Known processes are employed to prepare the cross-linked bead polymerizate used in the opaquer. These are described for example in the patents EP-B-11 190, EP-B-84 769, EP-B-11 735, EP-B-11 734 and U.S. Pat. No. 4,500,658 already mentioned above and the literature quoted therein in each case. It is important that the polymerization takes place in the presence of the coloured pigment, so that the latter is incorporated in the resulting beads when polymerization is complete.

Furthermore, the light-curing opaquer according to the invention contains polymerizable polyfunctional monomer (b). Coming into consideration for this purpose are polyfunctional (meth)acrylates used in dental materials. Particularly advantageous are ethylene glycol dimethacrylate (EGDMA), triethylene glycol dimethacrylate (TEGDMA), hexanediol dimethacrylate, 2,2-bis-4-(3-methacryloxy-2-hydroxy-propoxy)-phenylpropane (bis-GMA), urethane dimethacrylates formed by reaction of 2,2,4-trimethylhexamethylene diisocyanate with 2-hydroxyethyl methacrylate, decanediol dimethacrylate ($D_3MA$), butanediol dimethacrylate and the corresponding acrylates.

The quantity of cross-linked bead polymerizate, provided with coloured pigment, that is used must not be completely soluble in the quantity of monomer that is used. An initial dissolution of the bead polymerizate in the polyfunctional monomer (b) and optionally present monofunctional monomer (f) is however possible. Furthermore, it is undesired for the bead polymerizate to swell in the used monomers, since otherwise the viscosity of the opaquer would change too greatly. An increase in viscosity would mean, for example, that the opaquer composition could be pressed out only with great difficulty from the customarily used application syringes.

For the opaquer according to the invention to allow a colour match to natural tooth material in a broad range, it usually also contains white pigment (c1) and/or black pigment (c2) in addition to the coloured pigment. $ZrO_2$ and/or $TiO_2$ are preferably used as white pigment and carbon black pigment as black pigment. $ZrO_2$ is particularly preferred since it does not prevent through-hardening, even in very high quantities.

Furthermore, the opaquer according to the invention usually contains a photoinitiator (d) which catalyses the photopolymerization. In particular benzophenone and derivatives thereof as well as benzoin and derivatives thereof can be used for this purpose. Other preferred photoinitiators are the α-diketones, such as 9,10-phenanthrenequinone, diacetyl, furil, anisil, 4,4'-dichlorobenzyl and 4,4'-dialkoxybenzyl. Camphor quinone is particularly preferably used. Moreover, it is advantageous in many cases to use the photoinitiators together with reducing agents, for which purpose amines in particular, such as cyanoethylmethylaniline, dimethylaminoethyl methacrylate, triethylamine, triethanolamine, N,N-dimethylaniline, n-methyldiphenylamine, N,N-dimethyl-sym.-xylidene, N,N-3,5-tetramethylaniline and 4-dimethylaminobenzoic acid ethyl ester come into consideration.

Inorganic fillers can also optionally be present in the opaquer. In particular precipitated or pyrogenic silicas with an average primary particle size of 5 to 100 nm and a BET surface area of 0 to 400 $m^2/g$ are used for this purpose. Such materials are marketed by Degussa under the name Aerosil® or by Wacker under the name HDK®.

Finally, the opaquer according to the invention can also contain polymerizable monofunctional (meth)acrylic acid esters, in particular methyl methacrylate (MMA), hydroxyethyl methacrylate, tetrahydrofuryl methacrylate, cyclohexyl methacrylate, isobutyl methacrylate and the corresponding acrylates.

The opaquer composition according to the invention is prepared in the usual manner, in particular by thoroughly mixing the used components.

In particular, the procedure can be such that initially cross-linked bead polymerizate with an incorporated coloured pigment, for example red and yellow cross-linked bead polymerizates, are prepared. For this purpose, a premix of cross-linking agents with red or yellow colour pigments is mixed with methyl methacrylate, and peroxide is added to this mixture as a polymerization initiator. Polyfunctional methacrylic acid esters, such as urethane dimethacrylates and triethylene glycol dimethacrylate, are typically used as cross-linking agents. The polymerization is then carried out in a known manner in an aqueous phase as a suspension polymerization. The obtained red or yellow bead polymerizates are separated off, dried and screened. There usually then follows a tempering stage in order to destroy any residual peroxide present.

Colour pastes are then prepared using the thus-prepared red and yellow bead polymerizates. To this end, polymerizable polyfunctional monomer (b) and optionally other components, such as photoinitiator (d) and inorganic filler (e), are mixed with the bead polymerizates. The mixture is then usually homogenized on a triple-roll mill, whereby light-curable red and yellow colour pastes are formed. In order to match the colour of these pastes to the required colour of a natural tooth, they are mixed with conventional white and/or black colour pastes. These conventional white and black colour pastes are obtained by homogenizing polymerizable polyfunctional monomer, photoinitiator and inorganic filler with black pigments or with white pigments, in particular $ZrO_2$.

The light-curing opaquer according to the invention is advantageously suitable for covering metal structures in dentistry. For this purpose, it is applied in particular to the metal structures of dental restorations, such as bridges or crowns, and cured, and then usually a veneer, in particular a plastic veneer, is applied in the usual manner to the metal structure provided with the opaquer, thereby forming an aesthetically pleasant dental restoration.

It was surprisingly shown that, even with a high pigments content, in particular with $ZrO_2$ used as white pigment, and with a concomitant high covering power, the opaquer according to the invention can nevertheless be essentially completely cured with light. In contrast, conventional light-curing opaquers exhibit only a slight depth of through-hardening.

Furthermore, neither does the opaquer according to the invention tends to separation with formation of a filler-rich and a filler-poor phase, and therefore it is also suitable for extended storage.

Finally, the opaquer according to the invention also exhibits very good adhesion both to different metals which can form dental structures and to applied veneers.

Particularly advantageous quantities of the individual components of the opaquer according to the invention are given below, these being able to be chosen independently of one another:

(a) 2 to 20, in particular 2 to 15 and particularly preferably 3 to 12 wt. % of bead polymerizate with incorporated coloured pigment, (b) 20 to 70, in particular 40 to 60 and particularly preferably 50 to 52 wt. % of polymerizable polyfunctional monomer, (c1) 20 to 60, in particular 25 to 50 and particularly preferably 30 to 45 wt. % of white pigment, (c2) 0 to 0.1, in particular 0 to 0.01 and particularly preferably 0 to 0.005 wt. % of black pigment, (d) 0.1 to 6, in particular 0.5 to 4.5 and particularly preferably 1 to 3 wt. % of photoinitiator, (e) 0 to 20, in particular 2 to 20 and particularly preferably 5 to 6 wt. % of inorganic filler, and/or (f) 1 to 6, in particular 1.5 to 4.5 and particularly preferably 2 to 3 wt. % of polymerizable monofunctional (meth)acrylic acid esters.

The invention is explained in more detail below with reference to examples.

EXAMPLES

Example 1

Preparation of red and yellow cross-linked bead polymers

First of all, a base mixture having the composition below was prepared:

| Base mixture | |
| --- | --- |
| Urethane dimethacrylate | 3.0 g |
| TEGDMA | 0.530 g |
| Butyl cresol | 0.710 g |
| Silica (HDK H-15) | 0.350 g |
| Methyl methacrylate | 4.100 g |

This base mixture was mixed in each case separately with 1.1 g of a red iron oxide colour pigment (Siccotrans red) and 1.1 g of a yellow iron oxide colour pigment (Siccotrans yellow) respectively. Red and yellow bead polymerizates were prepared in a reactor using these mixtures according to the methods of suspension polymerization, that is accompanied by stirring and heat. The grain size was controlled by the polymerization parameters, and in the case of the prepared bead polymers it was below 32 μm.

Example 2

Colour pastes

The red and yellow bead polymerizates prepared in Example 1 were used to prepare red and yellow opaquer colour pastes according to the invention. Likewise, conventional white and black colour pastes were prepared. In each case, the individual components were mixed accompanied by stirring and homogenized in a triple-roll mill to form a paste. The individual red, yellow, white and black colour pastes had the following composition.

| | red (wt. %) | yellow (wt. %) | white (wt. %) | black (wt. %) |
| --- | --- | --- | --- | --- |
| bis-GMA | 44.6 | 44.6 | 42.9 | — |
| TEGDMA | 5 | 5 | 5 | — |
| HDK-2000 | 3.5 | 3.5 | 5 | — |
| Bead polymer | 40.0 | 40.0 | — | — |
| ZrO$_2$ | — | — | 40.0 | — |
| Camphor quinone | 0.7 | 0.7 | 0.9 | — |

-continued

| | red (wt. %) | yellow (wt. %) | white (wt. %) | black (wt. %) |
| --- | --- | --- | --- | --- |
| EMBO | 1.0 | 1.0 | 1.0 | — |
| Decanediol dimethacrylate | 5.2 | 5.2 | 5.2 | — |
| Carbon black pigment (microlith) | — | — | — | 30 |
| Colophonian resin | — | — | — | 70 |

The abbreviations used have the following meanings:
HDK-15 Microfine hydrophilic SiO$_2$, BET surface area 150 m$^2$/g
HDK-2000 Microfine hydrophobic SiO$_2$, BET surface area 170 m$^2$/g
EMBO p-dimethylaminobenzoic acid ethyl ester

Example 3

Preparation of opaquers

Different-coloured pasty opaquers were prepared using the colour pastes described in Example 2.

The quantities of the individual colour pastes were varied in the ranges given below in order to achieve a broad colour adaptability.

| Yellow colour paste | 6.4 to 24.0 wt. % |
| --- | --- |
| Red colour paste | 0.1 to 10.0 wt. % |
| White colour paste | 74.0 to 93.0 wt. % |
| Black colour paste | 0.5 to 4.5 wt. % |

In order to prepare the final opaquer, the individual colour pastes were weighed together and homogenized at high speed in an agitator. The obtained opaquers had a through-hardening depth which was clearly greater than that of comparable opaquers according to the state of the art.

For comparison with conventional opaquers, a reddish opaquer according to the invention was prepared, the colour of which is close to the colour code 540 of the Chromascop colour ring produced by Ivoclar, Liechtenstein. The white, red, yellow and black colour pastes described in Example 2 were mixed to this end.

A conventional opaquer of the same colour was prepared by mixing together white, red, yellow and black colour pastes to give a corresponding colour. The red and yellow colour pastes did not, however, contain any coloured bead polymerizates, but only the corresponding coloured pigments, namely iron oxide red and iron oxide yellow, were added.

A thin layer of both opaquers was then brushed onto metal, this layer was polymerized in a light-curing apparatus, namely a Spectramat from Ivoclar, Liechtenstein, for 2 minutes, a second, covering layer was applied and polymerization followed for a further 5 minutes in the light-curing apparatus. The opaquer layer was then scraped off with a probe.

In the case of the opaquer according to the invention, the lower layer was hard throughout and completely polymerized, whereas the conventional opaquer containing no bead polymerizate with incorporated coloured pigment had a soft and unpolymerized lower layer.

We claim:

1. A dental light-curing opaquer which comprises the following components:

(a) a cross-linked bead polymerizate into which a coloured pigment, but not a black or a white pigment, is incorporated, and (b) a polymerizable polyfunctional monomer, with the proviso that the quantity of (a) used is not completely soluble in the quantity of (b) used.

2. An opaquer according to claim 1, wherein the bead polymerizate (a) is based on at least one (meth)acrylic acid ester.

3. An opaquer according to claim 1, wherein the bead polymerizate (a) comprises 1 to 40 wt. % of incorporated coloured pigment, relative to the quantity of the bead polymerizate.

4. An opaquer according to claim 3, wherein the bead polymerizate (a) comprises 5 to 20 wt. % of incorporated coloured pigment.

5. An opaquer according to claim 3, wherein the bead polymerizate (a) comprises 10 to 15 wt. % of incorporated coloured pigment.

6. An opaquer according to claim 1, wherein the bead polymerizate has a degree of cross-linking of 10 to 90%.

7. An opaquer according to claim 6, wherein the bead polymerizate has a degree of cross-linking of 40 to 60%.

8. An opaquer according to claim 1, wherein the bead polymerizate has an average particle size of 10 to 100 µm, based on the number of particles.

9. An opaquer according to claim 8, wherein the bead polymerizate has an average particle size of 12 to 30 µm.

10. An opaquer according to claim 1 which comprises
    ultramarine blue; iron oxide pigments; coloured pigments based on cobalt, aluminum, chromium, nickel; zinc oxides; organic coloured pigments; or mixtures thereof as coloured pigments.

11. An opaquer according to claim 1 further comprising:
    (c1) white pigment or
    (c2) black pigment.

12. An opaquer according to claim 11, which comprises:
    $ZrO_2$ and/or $TiO_2$ as the white pigment and/or
    carbon black pigment as the black pigment.

13. An opaquer according to claim 1 further comprising:
    (d) a photoinitiator.

14. An opaquer according to claim 1 further comprising:
    (e) an inorganic filler.

15. An opaquer according to claim 1 further comprising:
    (f) a polymerizable monofunctional (meth)acrylic acid ester.

16. An opaquer comprising:
    (a) 2 to 20 wt. % of a bead polymerizate with incorporated coloured pigment, but not a black or a white pigment,
    (b) 20 to 70 wt. % of a polymerizable polyfunctional monomer,
    (c1) 20 to 60 wt. % of a white pigment,
    (c2) 0 to 0.1 wt. % of a black pigment,
    (d) 0.1 to 6 wt. % of a photoinitiator,
    (e) 0 to 20 wt. % of an inorganic filler, and
    (f) 1 to 6 wt. % of polymerizable monofunctional (meth) acrylic acid esters.

17. A method of covering metal structures of a dental restoration comprising:
    providing the dental light-curing opaquer according to claim 1;
    applying the dental light-curing opaquer on the metal structure; and
    curing the dental light-curing opaquer.

18. The method according to claim 17, wherein the metal structures are a dental bridge or a crown.

* * * * *